(12) United States Patent  
Ellis et al.

(10) Patent No.: US 8,580,560 B1
(45) Date of Patent: Nov. 12, 2013

(54) CAP WITH FILTER AND TRANSFER APPARATUS

(71) Applicant: Scientific Plastic Products, Inc., Oceanside, CA (US)

(72) Inventors: Samuel A. Ellis, Oceanside, CA (US); Kishan G. Hingorani, Oceanside, CA (US)

(73) Assignee: Scientific Plastic Products, Inc., Oceanside, CA (US)

( * ) Notice: Subject to any disclaimer, the term of this patent is extended or adjusted under 35 U.S.C. 154(b) by 0 days.

(21) Appl. No.: 13/715,666

(22) Filed: Dec. 14, 2012

(51) Int. Cl.
*C12M 1/00* (2006.01)
*B01D 25/00* (2006.01)
*B01D 24/46* (2006.01)
*B01D 29/46* (2006.01)

(52) U.S. Cl.
USPC ............. 435/297.1; 435/304.1; 201/232; 201/335; 201/350; 201/416.1; 201/436; 201/437; 201/488; 201/489

(58) Field of Classification Search
USPC ........... 435/297.1, 304.1; 210/232, 335, 350, 210/416.1, 437, 488, 489, 436
See application file for complete search history.

(56) References Cited

U.S. PATENT DOCUMENTS

| | | | |
|---|---|---|---|
| 4,415,449 A | 11/1983 | Hein | |
| 5,061,381 A | 10/1991 | Burd | |
| 5,064,531 A | 11/1991 | Wang et al. | |
| 5,076,933 A * | 12/1991 | Glenn et al. | ............. 210/335 |
| 6,605,216 B1 | 8/2003 | Lederman | |
| 6,713,299 B1 | 3/2004 | Sengoku | |
| 7,059,480 B2 | 6/2006 | Seshimoto et al. | |
| 7,125,434 B2 | 10/2006 | Yavorsky et al. | |
| 7,381,559 B2 | 6/2008 | Ellis et al. | |
| 7,709,251 B2 | 5/2010 | Ellis et al. | |
| 7,914,477 B2 | 3/2011 | Briggs et al. | |
| 7,967,152 B2 | 6/2011 | Muse et al. | |
| 7,998,730 B2 | 8/2011 | Ellis et al. | |
| 2005/0279695 A1 | 12/2005 | Straeffer et al. | |

\* cited by examiner

*Primary Examiner* — David A Reifsnyder
(74) *Attorney, Agent, or Firm* — Stetina Brunda Garred & Brucker; Lowell Anderson

(57) ABSTRACT

A cap has recess containing a porous frit and a graded porosity filter located so fluid from a container to which the cap is connected passes through the filter and out a spout on the cap. The filter porosity is selected to pass product expressed from cellular organisms grown in growth media inside the container while filtering out debris. A cap vent allows positive pressure in the container ullage to expedite filtering and reduce agitation of the container contents. This is not just a cap with a filter but an enabling tool. This tool enables total design change in many processes from previous thinking, allowing for the maximization of purified material, and reduction of multiple steps.

36 Claims, 6 Drawing Sheets

CAP WITH FILTER AND TRANSFER APPARATUS

CROSS-REFERENCE TO RELATED APPLICATIONS

Not Applicable

BACKGROUND

This method and apparatus are particularly useful for improving the extraction of products from extra cellular and intra cellular growth, especially for improving the extraction efficiency as to time and as to the quantity of material recovered. Various cells are grown in growth media with cellular products being extracted for use in various applications. Referring to FIG. 1, cells may be grown in containers having various shapes, with cells commonly grown in a growth flask or bio-reactor vessel 10 containing a growth media 12 and cellular material 36. One illustrative growth flask 10 is described in U.S. Pat. No. 7,381,559. If extra cellular growth is used the media 12 is selected to extract products 38 grown by and excreted through the cellular walls and into the media or otherwise extracted through the cellular walls and into the media, with subsequent processes separating the extracted products from the media and cells. If intra cellular growth is used, then a lysing agent is typically added to the media after growth is completed in order to rupture the cellular walls and allow the desired products to be separated from the media and ruptured cells in later processing. For either form of cellular growth, the process can be lengthy and result in product loss.

Still referring to FIG. 1, when growth is complete the fluid in the growth flask 10 is typically decanted into a storage container 14, sealed with cap 15 and can be stored until a sufficient quantity is collected for processing if the time permits, or if time is of the essence the fluid may be further processed immediately. Exemplary prior art means for transferring the contents of the flask 10 to a storage container or other container include the caps disclosed in U.S. Pat. Nos. 7,998,730 and 7,709,251

In decanting from the growth flask 10 to the storage container 14, the fluid may be transferred with or without filtering. The filtering seeks to separate the larger particles of the growth media and cells from the desired products and dissolved growth media which are smaller in size and pass through the filter. But some product is held by the filter or held by the debris collected on the upstream surface of the filter so that product is lost in the transfer. Typically, from about up to-20% of the product is lost in this filter step.

The material in the storage container 14, or from the growth flask 10, is ultimately placed in a centrifuge container 16 which uses centrifugal force from centrifuge 18 to separate the heavier cellular structures and larger particulate growth media from the desired product and dissolved growth media. The supernatant is removed from the centrifuge container 16 into a vacuum filter transfer flask 20. Because some of the product remains in the centrifuged cells and debris, about up to about 20% of the product is typically lost in the centrifuge separation. The vacuum filter transfer flask 20 has a neck with an opening that connects to a vacuum filter assembly 22 that is in fluid communication with a vacuum receptacle 24. Negative pressure is applied to the downstream side of the filter assembly 22 so that the product is drawn through the filter assembly 22 and into the vacuum receptacle 24. The filter assembly is selected to allow the product to pass while restraining passage of the cells, cellular fragments, and growth media which are larger in size than the product. If the filter becomes clogged by debris, then the remaining volume of fluid material in the vacuum filter transfer flask 20 is passed through successive filter assemblies 22 until all of the product is filtered into one or more vacuum receptacles. Each time a vacuum filter assembly 22 is used about up to 10% of product is lost. The filtered fluid from the vacuum receptacle is then passed through a purification column, such as a Resin filled purification column 26 in order to bind the growth media to the column and allow the purified product 38 to be separated therefrom, with the resulting fluid product being used for various purposes depending on the nature of the product. The purification column 26 may be a sterile column. About up to about 20% of the product is lost in the purification column 26 to achieve the purified product 38 from the purification cartridge 26, separated from the growth media 12 and cellular material 36.

Since a portion of product is lost each time the fluid is processed since several processing steps are used to purify the product, the total amount of product lost (either in absolute terms or percentage terms) can be extensive. Further, each processing step introduces errors through spillage, handling, contamination, and other human or machine error involved with each process step. Since it can take large amounts of time to grow the cells and their products, and since the extraction and purification process is also time consuming, the resulting cost of obtaining purified products is high in terms of time, effort and money. There is thus a need for a more efficient method and apparatus to separate the cellular products from the remaining cells, cellular fragments, growth media, etc.

The prior art uses tangential-flow filters, microfiltration filters, centrifugation, depth filtration and sterile filtration to help "clarify" the fluid between the various process steps, as described in the article by D. Yavorsky, R. Blanck, C. Lambalot and R. Brunkow, The Clarification of Bioreactor Cell Cultures for Biopharmaceuticals, Pharmaceutical Technology, March 2003, pg. 62-76, available at www.pharmatec.com. But even the use of various filters and centrifuges results in numerous process steps during which product is lost. There is thus a need for a more efficient method and apparatus and system to separate the cellular products from the remaining cells, cellular fragments and particles other than the desired product. Moreover, every human intervention step adds error and there is thus a need for an improved method, apparatus and system that reduces the number of human handling steps and human intervention steps.

BRIEF SUMMARY

An enabling cap and filtration assembly tool is provided that allows for maximizing the purified material from cellular cultures and permits reducing the number of steps in the traditional purification process. The cap and filtration assembly tool may include a cap that is placed on the neck of a container within which the product, cells, cell fragments and growth media are contained. The cap has a recess containing a porous frit and a graded porosity filter located so fluid from the container must pass through the frit and filter and out a spout on the cap. The filter porosity is selected and may vary per application or cell type to pass product expressed from cellular organisms grown in growth media inside the container while filtering out debris. A cap vent connected to a vent tube extending into the container ullage allows positive pressure in the container ullage to expedite filtering and/or reduces agitation of the container contents. Using filtration to separate product from the cells, cell fragments and debris works on a different separation principle (the size of the particles) than does using a centrifuge to achieve the separation and may entirely avoid the time consuming centrifuge step, and reduce the cost of expensive centrifuge equipment. The resulting product is believed to be sufficiently free of large particulates that the filtered fluid may be passed to a purification column in fluid communication with the spout of the cap and filter assembly tool, so that highly purified product may be produced by the purification column.

In more detail, there is advantageously provided a cap and filter step reduction tool for use in separating product excreted externally of living cells from liquids, larger particles of growth media and debris in which the product exists within a container. The container has a neck defining an opening to the container. The product is very small in comparison to the cells, with the product having a size measured by molecular weight. The cap has a first portion configured to cover the opening of the container, an outlet and a filter assembly located therebetween. The filter assembly includes a filter housing having a porous support with a rim around a periphery of the porous support. A graded porosity filter fits within that rim and has a small pore size sufficiently large to pass the product through the filter while retaining the debris and any larger particles of growth media, and sufficiently large and/or thick in the direction of flow to prevent clogging. A locking ring urges a periphery of the filter against an outer portion of the filter. A coarser porosity frit is located to place the filter between the porous support and the frit. The frit is sealed to the housing so fluid flows through the frit and to the filter during use.

In further variations, the cap has a vent opening extending through the cap with a vent tube connected to the portion of the cap defining the vent opening. The vent tube has a length selected to extend into an empty space (ullage) of the container when the container is inverted so that product flows from the container through the cap and filter step reduction tool. The vent opening may take the form of a tubular fitting extending from opposing surfaces of the cap. The vent tube avoids bubbles and thus not only prevents agitation of the contents during filtering but speeds up fluid flow. The potential damage to cells arising from the passage of bubbles should not be taken lightly. See, Y. Chisti, *Animal-cell damage in sparged bioreactors*, Tibtech, October 2000, Vol. 18, at pages 420-432 describes the mechanisms of cell damage from sparging bubbles in bioreactors. Further, a source of positive pressure may be placed in fluid communication with the vent opening so as to provide a positive pressure to the inside of the container during use of the cap and filter step reduction tool, thereby forcing fluid through the filter at a predetermined pressure.

The locking ring may have at least one annular rib around a periphery of the locking ring and located to abut an upstream surface of the filter during use. The cap may have at least one annular rib around a periphery of the cap and located to abut a downstream surface of the filter during use. The ribs force fluid through the filter and help prevent fluid flow around the outer periphery of the filter. Advantageously the filter assembly is press fit into a cylindrical recess in the cap formed by a cylindrical sidewall of the cap so as to seal the outer periphery of the assembly to the cap and further force fluid through the filter rather an around the periphery of the assembly. The cylindrical recess is preferably located downstream of a threaded skirt configured to threadingly engage the container so the cap can be removal fastened to the container. Preferably, the cylindrical recess has a flat, annular periphery with an inner portion that tapers to an outlet fitting forming the outlet therein so as to funnel the filtered product toward and out of the outlet fitting. Advantageously, an inner surface of the flat, annular periphery abuts the filter housing to provide a seat for positioning the filter assembly and sealing its periphery.

The filter may comprise a plurality of filters, each with a different discrete porosity and stacked together to form a graded porosity filter. Further, a stack of filters with the same porosity may be used, as may filters having a plurality of separate filters with a first porosity and a plurality of separate filters with a second porosity. A graded porosity filter is believed preferably and may have an interstitial pore spacing that decreases in the downstream direction of fluid flow during use.

The filtered product flowing out the outlet of the cap is advantageously placed in fluid communication with a purification column. A vacuum port downstream of the filter assembly may optionally be used in order to apply a negative pressure to the fluid in the container during use of the cap and filter step reduction tool. Preferably, the vacuum port is formed in the cap on the downstream side of the filter assembly, but the port could be placed in the fluid connection between the purification column and the cap.

The filters are preferably selected to pass product having a molecular weight from 10,000 to 3,000,000 MW, and more preferably to pass product having a molecular weight from about 100-150 MW. The filters and frit are selected to not only pass product of the desired size or molecular weight, but the filters are selected to be thick enough that they do not clog as the container is emptied. Thus, larger capacity containers may be larger sized filters, either in filter area (e.g., diameter) or depth or high binding capacity filters. The cap and filter step reduction tool may be used to filter various products, including products from any living cells, including mammalian cells or insect cells.

There is also provided a method of separating product excreted externally of living cells from liquids, larger particles of growth media and debris in which the product exists within a container. The product has a size small enough that it can be measured by molecular weight and the container usually has a neck defining an opening to the container. The method comprising the steps of fastening a cap over the opening of the container to form a fluid-tight connection and passing fluid contents of the container through a filter assembly in the cap. The filter assembly has a frit upstream of a graded porosity filter that has a small pore size selected to be sufficiently large to pass the product through the filter while retaining the debris. Typically, the growth media is small enough to pass through the frit but larger particles may be restrained from passage by the frit. The product thus passing through a cap outlet that is located downstream of the filter assembly. The method may also optionally include passing gas through a vent tube that is in fluid communication with ullage of the container located above the filter assembly.

In further variations, the step of passing gas through the vent tube applies positive pressure to the ullage of the container, or it may include applying a negative pressure downstream of the filter assembly to draw product through the filter assembly. The method may also include passing the product through a purification chromatography column.

There is also advantageously provided a for transferring fluid from a container having a neck defining an opening to the container where the container contains a product excreted externally of living cells that were contained in a growth media within the container. The container contains fragments of those cells. The product is small, having a size measured by molecular weight. The kit includes a cap having a first portion configured to cover the opening of the container, an outlet and a filter assembly located there between. The cap has a vent opening extending through the cap. A vent tube is provided having a first end configured to be connected to the portion of the cap defining the vent opening. The vent tube has a length selected to extend into ullage of the container when the container is inverted so product flows from the container through the cap. The filter assembly used in the kit includes several parts, including a filter housing having a porous support with a rim around a periphery of the porous support and a filter fitting within that rim and having a small pore size sufficiently large to pass the product through the filter while retaining the debris and optionally some growth media. The filter may be a graded porosity filter. The filter assembly may also include a locking ring urging a periphery of the filter against an outer portion of the filter and a frit located to place the filter between the porous support and the frit. The frit and locking ring are sealed to each other and to the filter housing so that fluid flows through the frit and then through the filter and out the cap outlet during use.

In further variations, the kit may include any of the above features described herein for use with the cap and filter assembly tool to transfer the product to the purification column. These features may include a first fluid transfer tube having one end configured to be connected to the outlet of the cap and a fluid flow control valve configured to be placed in fluid communication with the first tube either directly or through intervening fluid connections. These features may further include a second tube having a first end configured to be placed in fluid communication with a downstream end of the valve either directly or through intervening fluid connections, and having a second end configured to connect to one of a Luer lock or an inlet of a purification column.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 2:
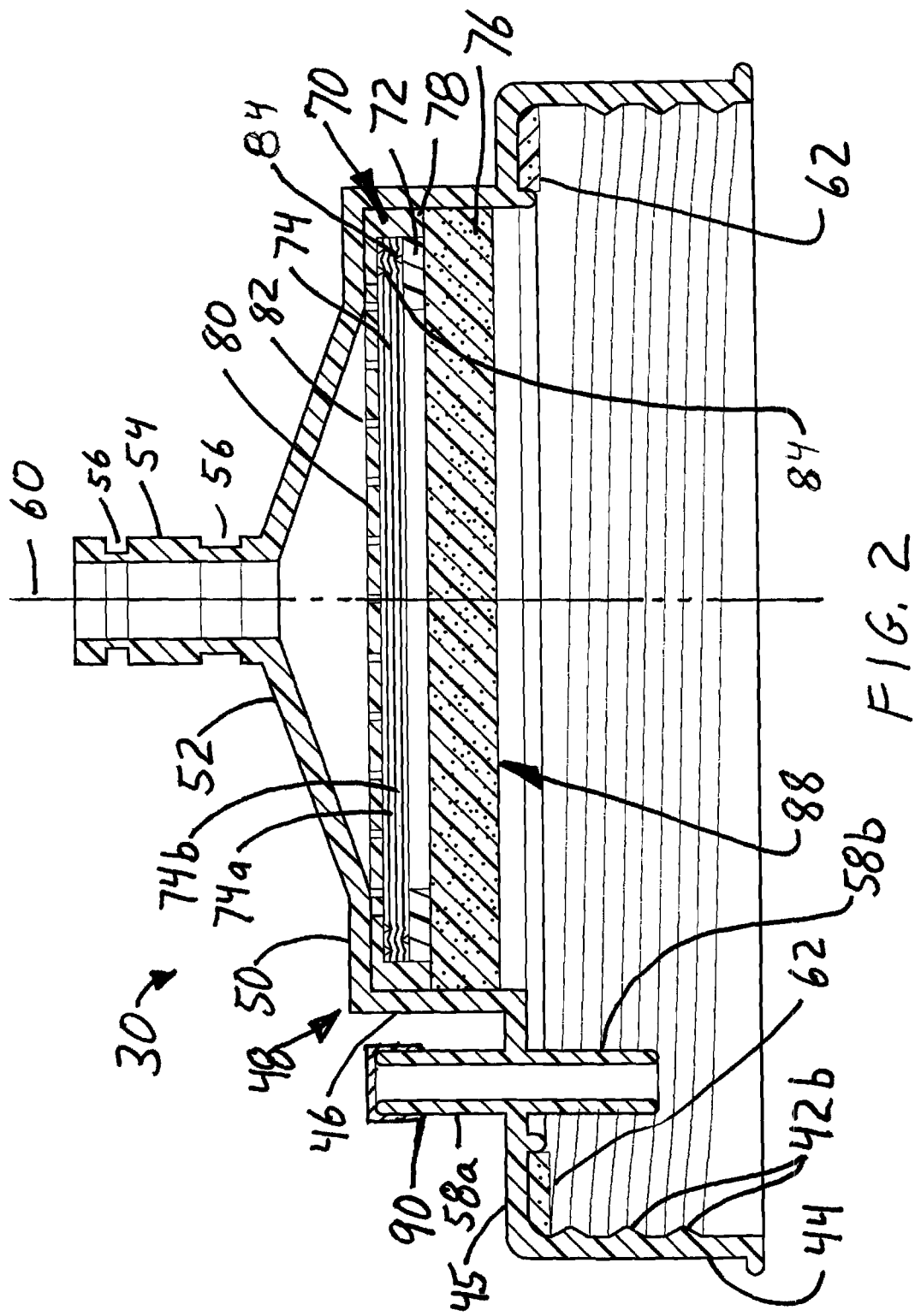
FIG. 2 is a cross-sectional view of a cap and filter step reduction tool.
Figure 3:
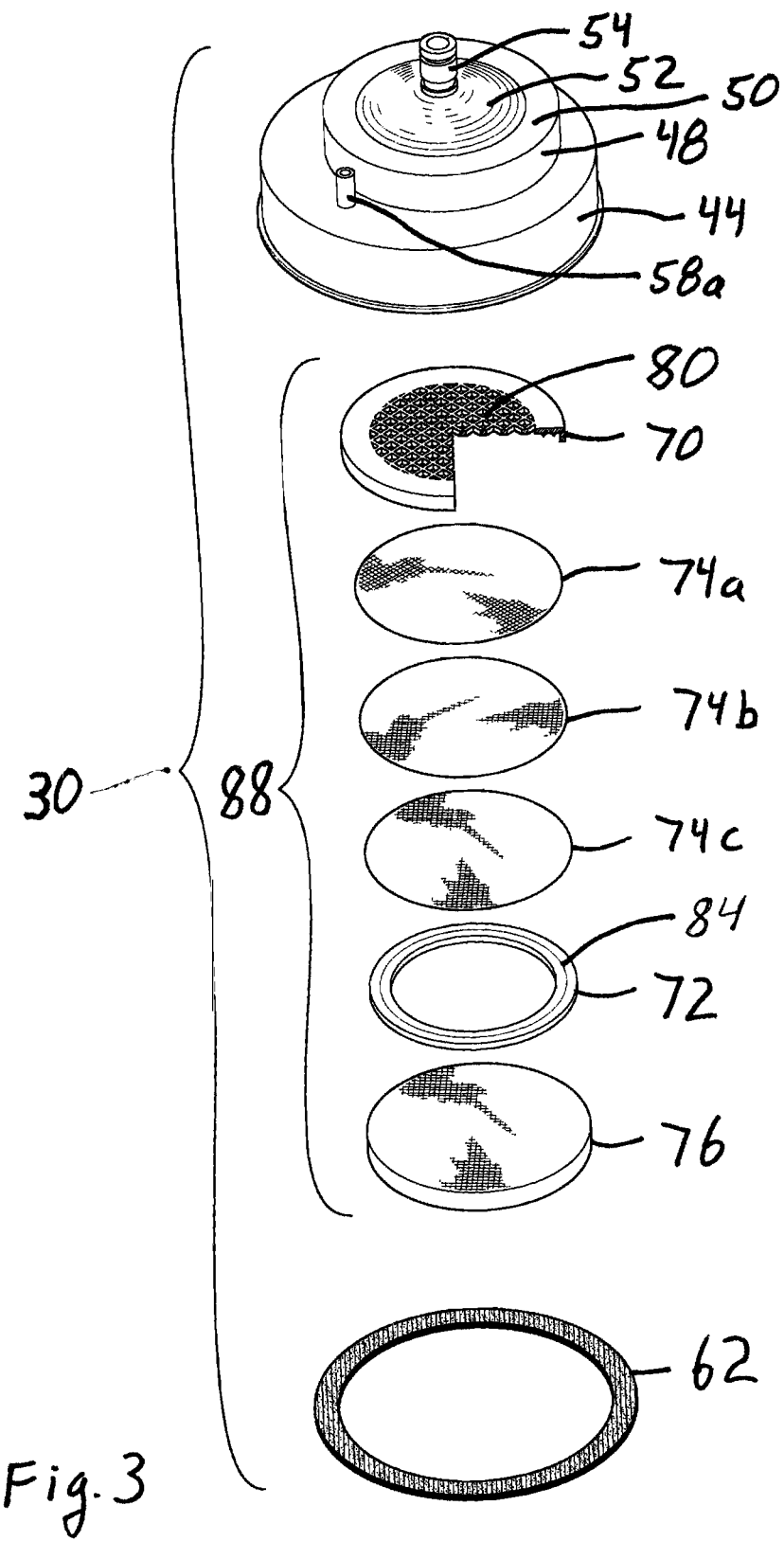
FIG. 3 is an exploded perspective view of the cap and filter step reduction tool of FIG. 2.
Figure 4:
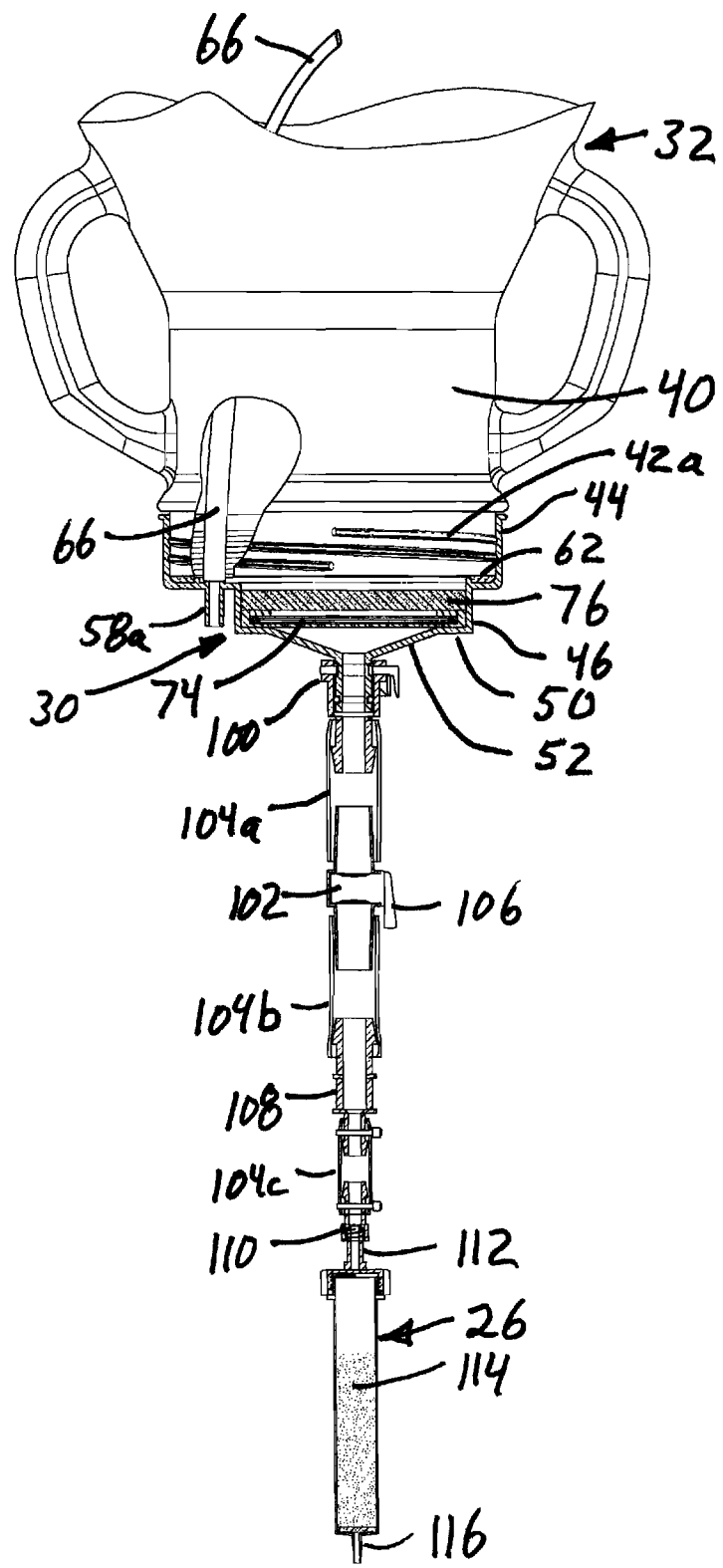
FIG. 4 is a partial cross-sectional view of the cap and filter step reduction tool of FIGS. 2 and 3 connected to a purification column.

Referring to FIGS. 2-4, a cap 30 is provided for a container 32 such as a growth flask 10, into which growth media 12 is placed along with cells 36 for cellular growth. The cells and media are selected for intracellular growth of products 38 or extracellular growth of products 38. The products 38 are smaller than the cells 36 and usually smaller than the growth media 12. The cellular material 36 may include microbial, mammalian, insect or other living cells from which products 38 may be made internal to the cells or excreted externally. Illustrative products 38 include proteins, antibodies, peptides, oils, lipids and amino acids. The container 32 typically has a neck 40 forming a fluid opening with the cap 30 fastening to the neck 40. In the illustrated embodiment screw threads 42a on the outside of the neck releasably engage with mating threads 42b on the inside of a cylindrical flange 44 of the cap to releasably fasten the cap to the container 32.

The cap 30 has a first top surface 46 with the flange 44 connected to an outer periphery of that surface 45. A stepped boss 48 extends from the first top 45 away from but the first top surface 45. The boss 48 has a sidewall 46 with a second top surface 50 enclosed by the sidewall 46. The sidewall 46 is preferably cylindrical but other shapes could be used. The second top surface 50 may have various shapes but is shown with an annular surface 50 parallel to first top surface 45. An inclined, preferably conical surface 52 extending therefrom. A tubular outlet fitting 54 extends from the conical surface 52, such that the cap 30 directs fluid to the inside of the boss formed by sidewall 46, with the tapered surface 52 directing that fluid toward and through the tubular outlet fitting 54 that is preferably offset from a longitudinal axis parallel to the outlet fitting 54 but through the center of the cap 30 and its skirt or flange 44. The exterior surface of the outlet fitting 54 may have one or more recesses 56 (FIG. 2) to receive annular seals, such as O-ring seals, D-ring seals, etc.

Figure 1:
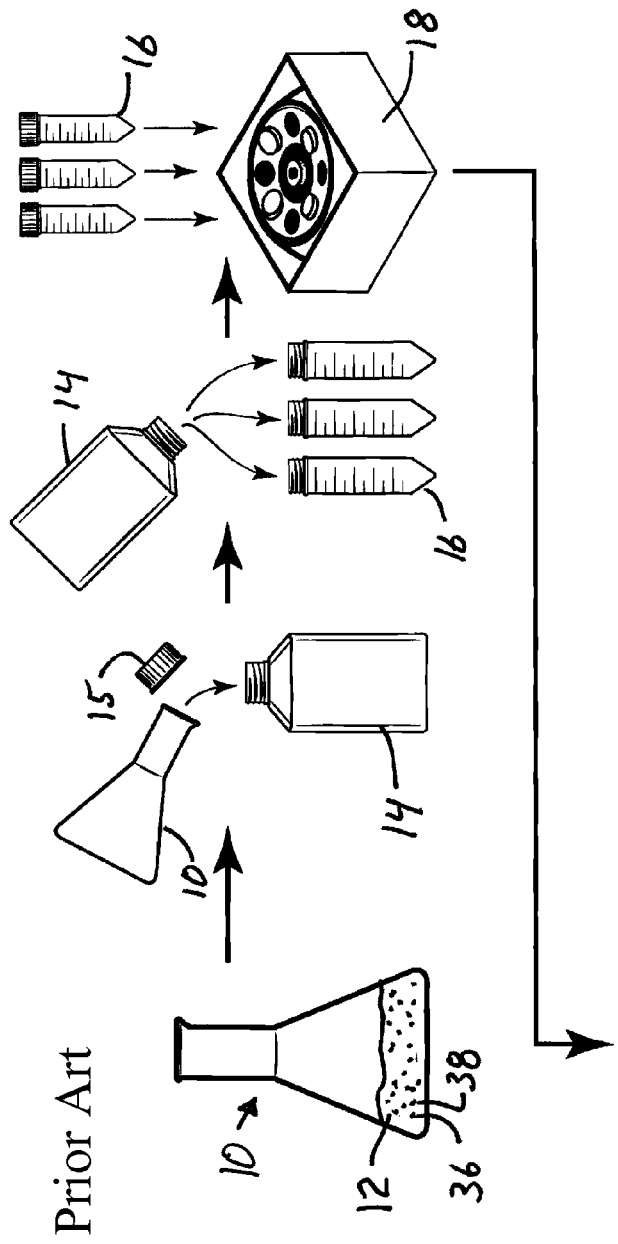
FIG. 1 is a flow schematic of a processing sequence of the prior art.
Figure 1:
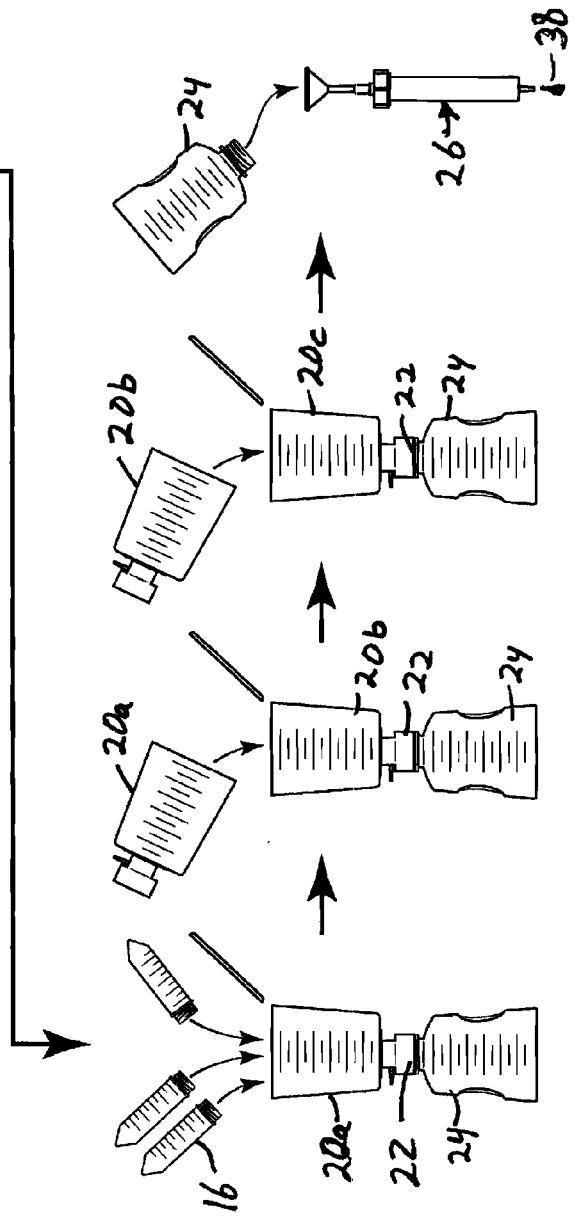

The second top 50 is formed on the boss 48 that is preferably offset from the cylindrical flange 44. The cap 30 has a vent fitting 58 extending through the first top surface 45 so that tubular vent fittings 58a, 58b extend from opposing sides of the first top surface 45. Advantageously, tubular vent fitting 58a is outside the cap 30 and vent fitting 58b is inside the cap. The fittings 58a, 58b are preferably aligned along an axis parallel to the longitudinal axis 60 (FIGS. 1, 6) through outlet fitting 54. A filter (not shown) is advantageously connected to the vent fitting to avoid introducing contaminants.

The interior surface of the first top surface 45 is optionally configured to receive an annular sealing ring 62 (FIG. 2). The depicted sealing ring 62 has a rectangular cross-section, but other shapes can be used. An annular projection 64 extends from the interior face of top surface 45 so the sealing ring 62 abuts the projection 64. A lip on the neck 40 of the container 32 abuts the sealing ring 62 to provide a fluid tight seal between the cap 30 and the container 32 during use, with the projection 64 helping to restrain movement and expansion of the sealing ring 62 to improve that fluid tight seal. The vent fittings 58a, 58b are preferably located inward of the annular projection 64 and sealing ring 62.

An elongated vent tube is connected to the passageway formed by vent fittings 58, preferably by fitting inside (FIG. 6) or over (FIGS. 4-5) the interior vent fitting 58b. The vent tube 66 extends a length sufficient to place the free end of the tube above the fluid level of the growth media when the container 32 is turned to place the neck 40 downward so as to pour the media out of the neck 40 through the cap 30 and outlet fitting 54. The vent tube 66 and passage formed by fitting 58b allow air to enter the ullage between the bottom of the container 2 and the fluid media 12 when fluid is transferred from the container 32 to another vessel. The air allows faster and smoother fluid flow through the cap 30 and outlet fitting 54, and it helps eliminate the bubbles which would occur if no air vent were allowed. Bubbles agitate the media 12, cells 36 and product 38 and can damage the cells 36 so that and reducing or eliminating bubbles them provides advantages.

Referring again to FIGS. 2-4, the inside of the boss 48 is configured to receive a filter assembly that includes a filter housing 70 with one or more filters 74 held in the housing by lock ring 72, and a frit 76 upstream of the filter assembly. As used herein, the relative terms upstream and downstream refer to the direction relative to a fluid flow from the container 32 to the purification column 26, during use of the filter apparatus and method. The filter housing 70 has a short, cylindrical sidewall 78 located around the periphery of a porous support 80. The support 80 is preferably planar but could be slightly inclined in a downstream direction, toward outlet fitting 54 as shown in FIG. 2. The porous support 80 has a plurality of openings 82 through which the filtered fluid from container 32 passes. The upstream end of the porous support 80 is preferably rounded on those parts that contact the filter 74 so the filter is not abraded, torn or damaged. Preferably, one or more annular sealing ribs 84 are formed in the support 80 adjacent the flange 78, with the projections extending toward the filter 74. The sealing ribs 84 form projections that seal against the filter 74 to prevent fluid from passing radially outward past the ribs 84 and between the peripheral edges of the filter 74 and housing 70. The frit is in sealing contact with one or both of the lip on the periphery of the sidewall 78 or the locking ring 72 so as to force product 58 through the frit 76 and toward the filter 74 during use, and to inhibit product from flowing between the frit and sidewall 78, and between the sidewall 78 and the locking ring 72. The sealing contact is advantageously obtained by press fitting the filter housing 78 and frit 76 into the recess formed by the sidewall 46 of the cap 30, but other sealing means can be used, including adhesives, melting, of sealing rings interposed between the parts. Further, the lock ring 72 and frit 76 are advantageously sized relative to each other so the ring 72 abuts the frit 76 to form a fluid tight seal around a periphery of the frit.

The filter 74 is held in the housing by a retaining part which takes the form of an annular retaining ring 72 when the filter 74 is a planar filter or sheet. If the filter 74 is formed of loose granules then the retaining part will comprise a porous support similar to support 80, with openings sized to retain the filter material. The term retaining lock ring 72 will be used to refer to either the annular construction or the porous support construction unless noted otherwise.

The retaining ring 72 has a periphery configured to form snap fit connection with the sidewall 78. Advantageously, the sidewall 78 may be shaped to have a surface facing the ring 72 which surface is inclined so as to retain the retaining ring 72 and form a snap fit connection. An inclination of about 5 degrees is believed suitable. Alternatively, a slight projection can on the edge of the sidewall 78 may be used to form a snap-fit connection between the sidewall 78 and the retaining ring 72 in order to hold the parts together during assembly and use. Mating screw threads could also be used for a removable connection. Permanent fastening devices such as sonic welding, adhesives, staking, plastic deformation, or an interference fit in the parts may also be used to form more permanent connections. The retaining ring 72 holds the filter 74 in position against the porous support 80.

Referring to FIG. 3, the retaining ring 72 is shown as an annular ring with a rectangular cross-section. Preferably, one or more annular sealing ribs 84 are formed ring 72, adjacent the flange 78 during use, with the rib extending toward the filter 74. The sealing ribs 84 form projections that seal against the filter 74 to prevent fluid from passing radially outward past the ribs 84 and between the peripheral edges of the filter 74 and housing 70. Advantageously, the locking ring 72 has one rib 84 located to abut the filter 74 opposite and between two ribs 84 located on the porous support 80. But different arrangements may be used.

The frit 76 may be a polymer or glass frit customary in such applications. A frit about 1/16 to 1/2 inch thick is believed suitable, but the thickness will vary with the specific use. The frit 76 is preferably selected to be stiff enough to prevent the filter housing 70 from buckling and forming an incomplete seal with the inside of sidewall 46 and/or the inside of annular surface 50. The housing 70, filter 74, retaining member or ring 78 and frit 76 form a filter assembly 88 (FIG. 3) with is held in the cap 30, preferably by being press fit into the cylindrical recess formed by sidewall 46. The filter assembly 88 may retained by other mechanisms, such as snap rings, threads, deformation of materials, etc. The filter assembly 88 may be removably retained in the cap 30, or permanently fastened thereto as by a tight interference fit between one of the frit 76 or housing 70 and the adjacent sidewall 46.

The filter 70 may comprise one or more separate filters, but preferably has less than about 10 filters. Filters 74 of polypropylene, nitro cellular material, PVDF, polytetrafluoroethylene, Nylon, glass or glass fibers are believed suitable. Preferably, multiple filters are used with each filter being of a different porosity and with the larger porosity filter located upstream and the smaller porosity filter located downstream so as to provide a graded porosity filter with the pore size or interstitial spacing between parts of the filter decreasing in the direction of flow. FIG. 2 shows two filters, 74a, 74b, with filter 74a being the downstream filter of smaller porosity than upstream filter 74b, while FIG. 3 shows three filters 74a, 74b, 74c. There is thus provided a depth filter with the pore size decreasing in the direction of flow, although the pore size could increase in the direction of flow. The particular porosity and combination of pore variation will vary with the particular use. The smaller pore size of the filter 74 should be sufficient large to pass the product 38 and sufficiently small to retain the cells 36, cell fragments and larger particles of growth media 12. A single graded porosity filter 74 may be used, or a plurality of filters 74 of a fixed but different porosity may be stacked together, and variable porosity filters having different porosity (large v small pore sizes) may be stacked together.

The porosity of the filter 74 will vary with use. The pore sizes are preferably selected to allow filtering of the entire contents of the container 32 in one use, and preferably with a few uses and ideally with no more than two or three uses, each use with a new cap 30 and/or filters 74.

The size of most commonly used cells 36 may vary from about 10 micrometers to 0.2 micrometers, but during processing the cell walls are ruptured intentionally or accidentally so as to generate smaller-sized cell wall fragments which must be removed from the product 38. The products 38 may advantageously sorted or filtered by molecular weight. Thus, for example, filters 74 suitable for separating product 38 comprising proteins will accommodate passage of molecules of about 100,000 to 3,000,000 MW, while filters 74 suitable for separating products 38 comprising peptides or amino acids will accommodate molecules of about 100-10,000 MW, while filters 74 suitable for separating products 38 comprising lipids will accommodate molecules of about 1 million MW to 10 million MW, of product 38 of about 100-10,000 MW. Oils may have even larger variations in molecular weights. Within those ranges, the particular filter 74 will vary depending on the specific product 38 and its associated molecular weight or size of molecule associated with that specific product 38.

To increase the capacity of the fluid and product 38 that may pass through the filter 74 and frit 78 before clogging reduces the flow to an unacceptable extent, it is desirable to have a large area of the filter and frit and, for depth filters, to have a sufficiently thick filter and frit (measured in the direction of flow) so as to prevent clogging. The precise area and thickness will vary with the type of product 38 and cells 36 involved, and with the volume of the container 32 which determines the volume of product passing through the filter and frit. Likewise, the porosity may affect the purity of filtered product 38 since some debris may pass through the frit 78 or filter 74 of the pores are large enough relative to the debris size. Further, filters and frits are not made with specific sized pores or passageways as there is some variation arising during manufacturing.

In order to achieve a larger filter area the neck 40 and opening of the container 32 may be increased, allowing a larger cap and filter step reduction tool 88 within the cap 30. But the vent tube 58 prevents the filter and frit from occupying the entire area within the skirt 44 of the cap. Thus, the axis 60 of the outlet 54 is offset from the longitudinal axis of the cap 30 and its skirt or flange 44. The longitudinal axis 60 is preferably the longitudinal axis of recess for the boss 48, filter 74 and filter assembly 88. Further, the vent fitting 58 may have the vent tube 66 or a positive pressure tube (not shown) connected to the outside of the tube so a slight space is left between the vent tube 58 and the sidewall 46 of the recess into which the filter assembly 88 is placed.

In use, the cells 36 and growth media 12 are placed in a growth container 32 and maintained under suitable temperature and other relevant environmental conditions to cause cellular growth and production of a desired product 38 by cells 36. For extra-cellular growth the product 38 is excreted from the cells 36 into the surrounding fluid media 12 or is extracted by chemicals in the surrounding fluid media 12. For inter cellular growth the product 38 remains inside the cells until harvesting, at which time the cell walls are ruptured, as for example by lysing. The cap 30 and filter assembly are then fastened to the container 32, preferably by screwing the cap onto the threaded neck 40 forming the opening to the container.

The container 32 and cap 30 are then tipped to pour the container contents through the cap and its filter assembly 88. The frit 76 blocks larger particles, with the filter 84 blocking smaller particles while allowing the product 38 to pass. The frit 76 and filter 74 are configured to allow passage of the product 38 while blocking the larger particles so as to separate out the larger particles of media 12, cells 36 and cell fragments. The porous support 80 helps support the filter 74 during use with the openings 82 allowing passage of the product 38. The product 38 is directed toward outlet fitting 54 by inclined wall 52. Advantageously, the filter assembly 88 is configured so that the entire contents of the container 32 may be filtered by one filter assembly, without clogging the frit 88 or the filter 74, while still producing an effluent containing highly pure product 38 and low or no content of unwanted material such as debris containing cell wall fragments or larger particles of media 12.

The cap 30 advantageously has a vent tube 66 selected to be long enough to reach the ullage of the container as fluid flows through cap 30. The containers 32 are typically from 20-60% full of fluid and as the container 32 is tipped to place the container bottom above the cap 30, the fluid flows toward the cap 30 and the air moves toward what used to be the bottom of the container. When the container 32 is tipped the end of the vent tube 30 enters the air-filled space and allows air to enter the ullage between the container contents and the bottom of the container which is now above the cap 30. Allowing air to flow through the vent tube 66 allows several advantages. Little fluid will flow out of a rigid walled container unless the fluid volume is replaced by gas, such as air. Allowing air flow through the vent tube 66 eliminates bubbles which pass through the fluid media and can not only agitate the media and cells but can generate further cell fragments. It also allows for a smoother flow of fluid through the cap 30 and outlet fitting 54 thereby allowing filtering with the generation of fewer cell fragments and debris. It further allows filtering of debris and separation of the product 38 in a single step, thereby not only shortening time significantly, but improving the yield by eliminating several process steps used in the prior art. The air or other gas flowing through vent tube 66 is preferably filtered to ensure any contaminants are removed before entering the container 32, or the gas may be provided from a source known to free of contaminants.

Because the vent fitting 58a is open to air, as the container 32 is tipped to pour fluid out the cap 30 and its outlet fitting 54, some fluid may enter the vent tube 66 and that fluid may flow out the vent fitting 58, as may any additional fluid entering the free end of the vent tube 66 as the container is tipped. A removable cap 90 (FIG. 2) may thus be provided on the exterior vent fitting 58a to seal that end of the vent line and reduce the volume of fluid entering the open, free end of the vent tube 66. Once the container 32 is tipped and the free end of the vent tube 66 is in the empty space between the container bottom and the fluid in the container, then the cap 90 may be removed. The cap 90 is optional.

Figure 5:
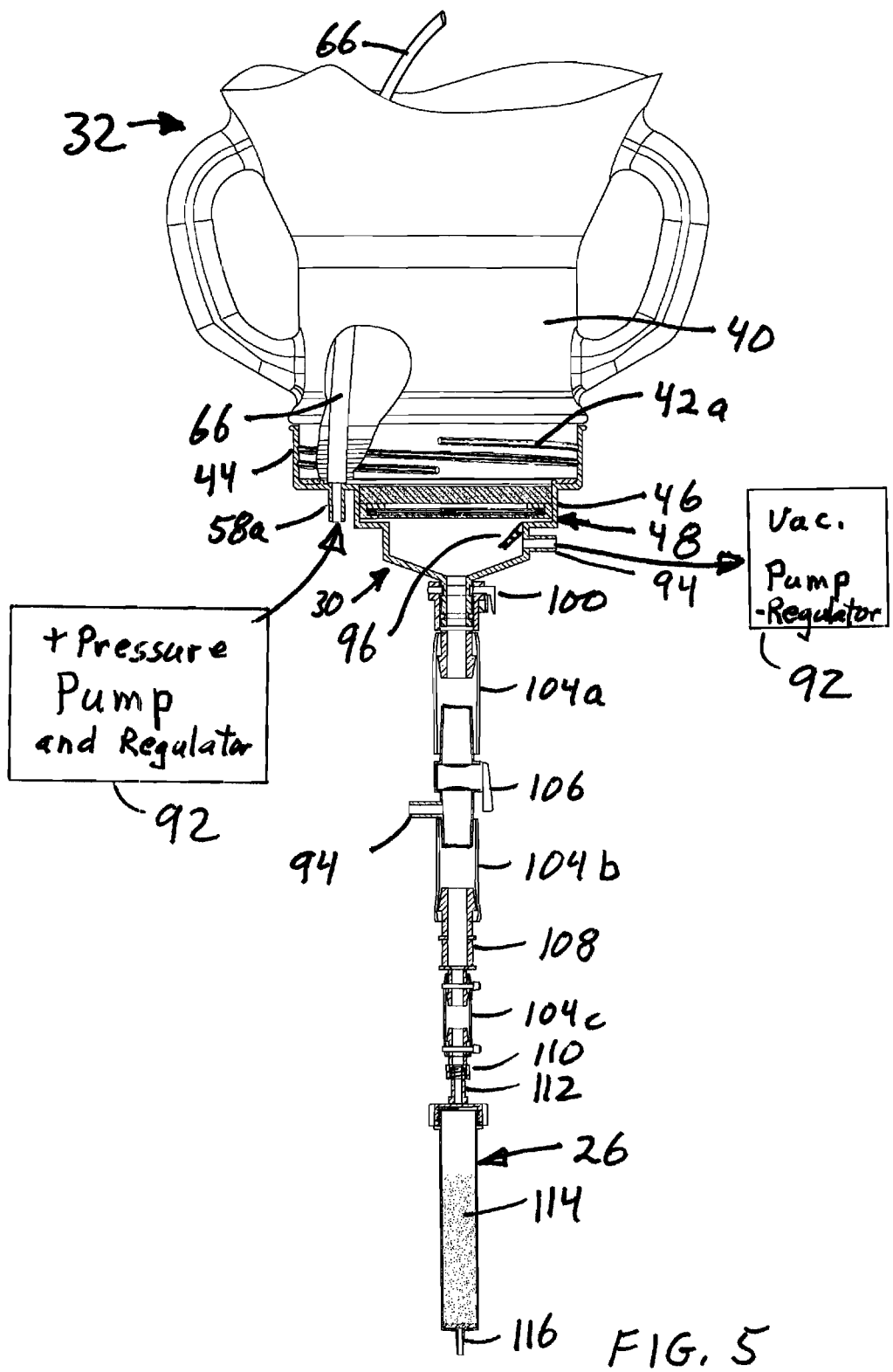
FIG. 5 is a partial cross-sectional view of the cap and filter step reduction tool of FIGS. 2 and 3 connected to a purification column, with vacuum ports on the cap and fluid transfer tubes.
Figure 6:
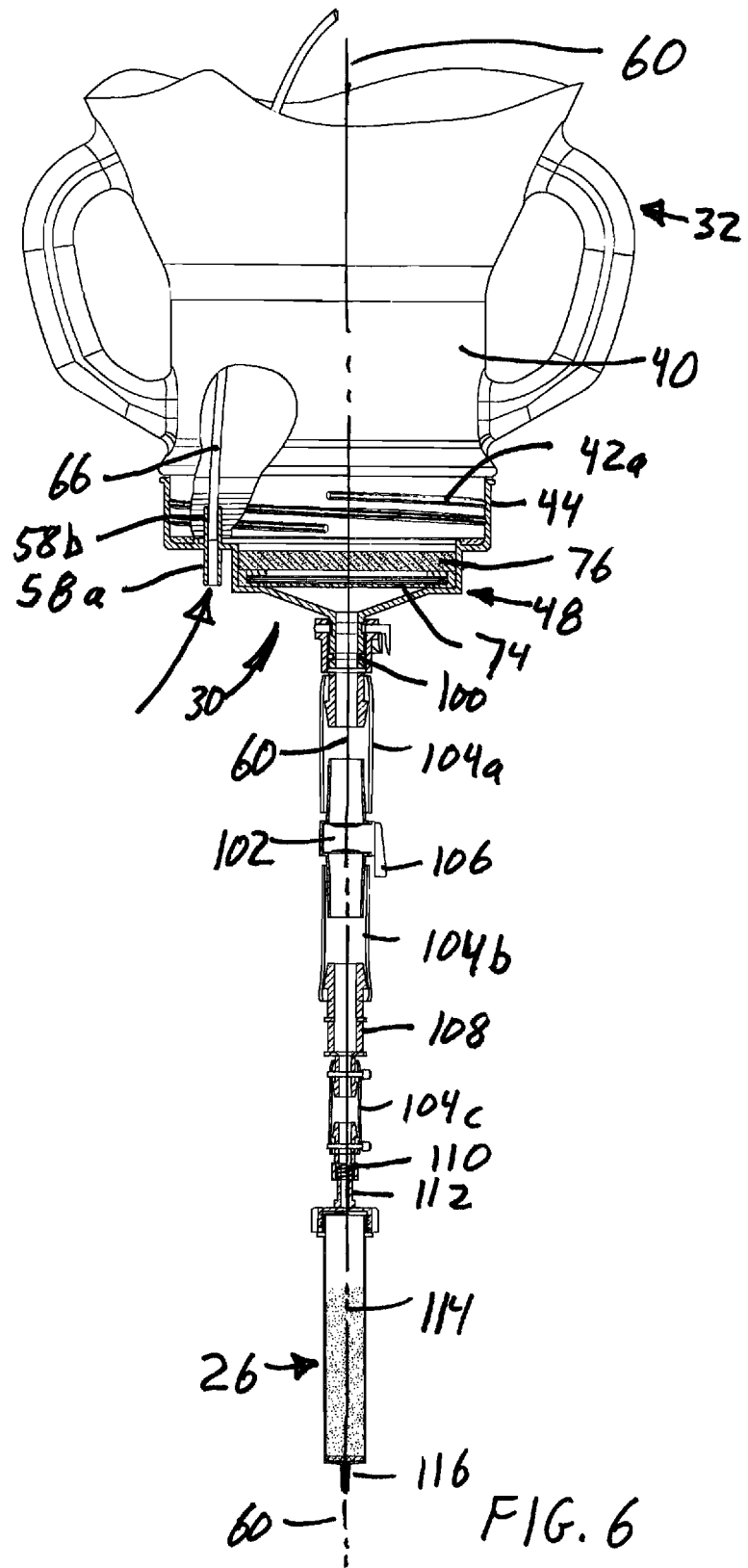
FIG. 6 is a partial cross-sectional view of the cap and filter step reduction tool of FIGS. 2 and 3 connected to a purification column, with the vent tube on the inside of a vent fitting.

Further, referring to FIGS. 4-6, by applying positive pressure to the vent fitting 58, a positive pressure can be provided in the air space between the container and the fluid inside the container so as to force the container contents through the cap 30, filter assembly 88 and outlet fitting 54. A filter (not shown) is advantageously provided between the source of positive pressure and the ullage in the container 32 so as to prevent contaminants from entering the container, or a gas source known to be free of contaminants may be used. If the positive pressure is applied by hand, a syringe filter may be used to provide filtered air to the container 32 through the vent 58. The positive air pressure on the upstream side of the filter assembly 88 pushes the fluid through the cap 30 and filter assembly 88 faster, thereby further reducing the time to process the contents of the container 2 and separate out the product 38. A hand squeezed bulb or a bellows, including a pleated, accordion-type of bellows may be used manually to provide positive pressure. Indeed, any manually generated pressure source may be used. Likewise, other sources of positive pressure may be used, including air pumps, canned gasses (air, inert gases or other gases), nitrogen generators, and other gas sources may be used.

Preferably, but optionally, the amount of positive pressure may be controlled so that the pressure does not force fluid through the filter assembly 88 so fast that it causes further and unacceptable generation of debris, or so that it causes an unacceptable reduction in purity of product 38, or so fast that it exceeds the binding capacity of downstream components, such as purification columns. Thus, a pressure regulator, pressure gage, or pressure limiter 92 may advantageously, but optionally be provided in fluid communication with the source of positive pressure and the vent inlet fitting 58a.

Optionally, and referring to FIG. 5, a cap 30 having vacuum port 94 may be used to apply a negative pressure or suction to the downstream side of the filter assembly 88, thus drawing fluid through the filter assembly 88 faster. In order to prevent filtered fluid and product 38 from being drawn into the vacuum port 94, a baffle 96 is interposed between the port 94 and the fluid flow path along which fluid exits from the filter 74 toward outlet fitting 54. The negative pressure is selected so that the force of gravity on the filtered fluid exceeds the force exerted by the vacuum port, allowing the filtered fluid to flow out the outlet fitting 54.

The outlet fitting 54 may be in fluid communication with various devices, including fluid containers or other processing equipment. Referring to FIGS. 4-6, the outlet fitting 54 of cap 30 is connected to releasable connector 100 sealingly engaging with recesses 56 or seals within recess 56 to provide a fluid tight connection. The connector 100 preferably comprises a Coulder connector or other type of locking connector. The connector 100 has a distal end with a tapered, flanged end that is sealingly connected to valve 102 of first tubular connector 104a. The valve 102 may be any type of actuatable valve, manual, electric or pneumatic. Valve 102 is depicted as a rotating ball valve that is actuated manually by valve lever 106. As shown in FIG. 5, a vacuum port 94 may be provided between the cap 30 and the purification column 26 in order to urge the fluid and product 58 through the filter assembly 88. FIG. 5 shows the vacuum port 94 on the downstream end of the valve 102, but it could be located on other parts or have its own connection. Baffles 96 (not shown in FIG. 5, are provided as needed.

An optional step-down connector 108 is connected to the downstream end of valve 102 by second tubular connector 104b. A further and optional step-down connector 110 having a Luer lock fitting may be connected to the downstream end of the connector 108 by third tubular connector 104c. The Luer lock fitting 110 connects to the inlet fitting 112 of further purification devices, such as a chromatography column or purification column 26. The purification column 26 is shown with a tubular body containing media 114 and outlet 116 through which the purified product 38 flows. Column 26 may be a flash chromatography column.

In use, the container 32 is tipped upside down and held (manually or by a suitable support frame) so the contents of the container 32 are forced by gravity and/or pressure from tube 66 through the filter assembly 88 of cap 30, through outlet fitting 54. The valve 102 regulates the flow and preferably is adjustable to allow varying the flow rate. As needed, the one or more step-down connectors 108, 110 conform to the fluid connection of the cap outlet 54 to the inlet fitting 112 of the purification column 26. The filter assembly 88 removes the unwanted cells 36 and larger particles of media 12 in a single filtration unit, and provides the filtered product 38 to the purification column 26 through one or more fluid communication tubes, with the column 26 removing or binding any growth media and unwanted particles to provide highly purified product 38 from the outlet 116 of purification column 26. The purified product 38 from the column 26 is collected for further use that varies with the nature of the product 38 being produced within the container 32.

By using a filtration assembly 88 having a coarse filter or frit 76 and a downstream graded porosity filter 74, the product may be more efficiently separated from the unwanted debris within the container 32 in a single filtration step. By selecting the porosity of the filter 74 to pass only the product 38 and by using graded density filtration the filter assembly 88 may avoid clogging. A single step filtration is much more efficient than multiple filtration and transfer steps which lose about up to 20% of product with each step.

The filtration time will vary with the nature of the product 38 and growth media 12, but a filtration time of about 3 hours (without positive pressure through tube 66) for a 2-5 liter container 32 holding about one liter of growth media (*e-coli*) and product (plasmid+) has been achieved, using a 2.5 inch (63 cm) diameter filter 74 and ⅛ inch (0.3 cm).

This filtration process and method are believed applicable to containers 32 of various sizes. Current growth containers vary from about 1 milliliter to 200 liters, with the growth media typically filling from 20-60% of the container volume.

But the filter assembly 88 and cap 30 may be configured as needed to accommodate various containers sizes and shapes, and to accommodate atmospheric or positive press (above atmospheric pressure) through vent tube 66. By configuring the cap 30 to hold the filter assembly 88, a simplified apparatus is provided for use in the filtration method provided by use of the cap. The prior art method required growing the product 38 in media 12 within containers 32, decanting the liquid, storing it for bulk processing (if time permits), centrifuging it, vacuum filtering it one or more times, and then running it through a purification column 26. The present method goes straight from the growth container 32 to the purification column 26, eliminating numerous steps and eliminating the loss of product 38 that typically accompanies each transfer step in the prior art process. There is thus provided a simpler process, a faster process, a more efficient process and a less costly process.

Moreover, the prior art separation by centrifuge forces the cell remnants against one another and compresses them with a force that varies with the centrifuge speed and radius. The, the filter assembly under gravity flow is a gentle separation, and even with a positive or negative pressure to increase the flow through the filter, the force on the separated cells is believed to be lower than the force applied by a centrifuge. The cells can be removed from the filter and frit by scraping them off, and if desired, by back flowing fluid or gas through the filter and frit. The cells removed from the filter assembly 88 may thus be recovered. The recovered cells may be reused, as for example, by placing them in a growth media in a different container for use in a process that uses cellular fragments. There is thus provided a method and apparatus for collecting cells and cell fragments on a frit, filter or filter assembly, and recovering the cell fragments by removing them and as desired backwashing the frit, filter or filter assembly, and providing cells and cell fragments for reuse in another applicator, and for reusing such cells and cell fragments.

The filter 74 and filtration unit 88 are provided in a single housing (cap 30) and are preferably designed to form a single use, disposable unit. Likewise, the parts placing the cap 30 in fluid communication with the purification column 26 are preferably provided either as a single unit, or as separate parts of a kit, preferably with the cap 30 (and filter 74 and assembly 88), or provided already connected to the outlet of cap 26.

In light of the current disclosure and cited references one skilled in the art would be able to devise suitable filters 74 and filter assemblies 88 without undue experimentation, for various processes, some of which are discussed below. For example, a plurality of filters in a substantially planar, disk-stacked design, or in a lenticular stacked-disk cartridge design is believed suitable for depth filter assembly 88. Filters with cellulosic fibers of different grade are believed suitable, with a membrane prefilter layer being optional on any of the filters 74 or filter assemblies 88. The above identified article by Yavorsky, Blanck, Lambalot and Brunkow, titled The Clarification of Bioreactor Cell Cultures for Biopharmaceuticals, Pharmaceutical Technology, March 2003, pg. 62-76 describes various factors for selecting depth filters in prior art applications applying various pressures and flow rates may be applicable to the filter 74 and filter assembly 88, and the contents of that article are incorporated herein by reference. U.S. Pat. No. 7,125,434 describes a depth gradient density filter with a pre-filtration zone retaining particles of about 25 microns to about 1 micron, a primary filtration zone retaining particles in the range of about 0.3 to 1 micron, even at a fluid velocity of about 100 cm/hr or more and an initial hydraulic permeability of greater than about 10 cm/hr/psi and such filters are believed suitable for use herein. That patent also describes depth filters with three zones each configured to retain particles of a different size distribution range (from about 25 microns to 0.2 microns total range) but that patent describes a pre-concentration zone device and that type of device relies on repeated recirculation of the fluid through the filters in order to retain a significant portion of the debris in the filtered fluid. This approach of using repeated passage through the same filter(s) contrasts with the presently described method, system and apparatus which is preferably a one-time flow device, with no pre-concentration zone, and having an area where the cells 36 and debris are totally separated from the cells 36 and debris and with the purified product 38 produced at the end of the process and system, via purification column 26. Thus, the present method, apparatus and system preferably does not use pre-concentration. Instead, the media 12, cells 36 and product 38 are passes through the cap 30 and its filter 74 filter a single time and clarified sufficiently so the resulting fluid may be passed to the purification tube 26 which produces highly purified product 38.

Further, that patent also uses fast flowing depth filtration device or tangential flow device. The present filtration apparatus, system and method will have a more limited flow when in fluid communication with a purification column 26, typically with a maximum flow of about limitation of 20-25 cm/hour, due to the binding coefficient of the filtration column.

U.S. Published patent application 2005/0148846 describes a stack of spaced-apart depth filters held by end plates and preferably embedded in a thermoplastic framework to create a disposable filter, with the end plates causing the fluid to pass through one or more of the plates substantially contemporaneously (i.e., in parallel) before exiting the filter assembly. This structure is also believed suitable for use herein although the increased length to accommodate the spaced-apart stacked filters may require a more noticeable increase on the size of the cap 30. The contents of U.S. Pat. No. 7,125,434 and published application 2005/0279695 are incorporated herein by reference. Given these disclosures and the present description, suitable filters and filter assemblies for the apparatus and processes disclosed herein are believed available without undue experimentation.

Exemplary processes believed suitable for using the apparatus described herein include the use of growth media 12 to produce product 38 containing proteins which are purified using the filter assembly 88 of cap 30. Mammalian cells 36 (e.g., CHO, HEK, HeLa, etc.) may be used to produce product 38 comprising various antibodies. CHO cells 36 secrete products that include proteins 38 out of the cell and the resulting antibiotics from the products 38 include commercial antibiotics products sold under the trademarks Avastin® and Aransep®. CHO cells are believed to currently be the most widely used mammalian cells in biotechnology manufacturing, and are employed to make top-selling medicines such as Amgen Inc.'s anemia treatment product sold under the trademark Aranesp® and Roche Holding AG's cancer drug sold under the trademark Avastin®.

Thus, the method and apparatus described herein are believed suitable for using cells 36 that include fungi, such as *Bacillus, Aspergillus* and *Trichoderma*, which fungi are believed suitable for use in producing product 38 that includes various enzymes. One desirable enzyme is α-Amylase which is an enzyme EC 3.2.1.1 that hydrolyses alpha bonds of large, alpha-linked polysaccharides, such as starch and glycogen, yielding glucose and maltose. α-Amylase is the major form of amylase found in humans and other mammals. It is also present in seeds containing starch as a food reserve, and is secreted by numerous fungi. α-Amylase is also used in ethanol production to break starches in grains into fermentable sugars. The first step in the production of high-fructose corn syrup is the treatment of cornstarch with α-amylase, producing shorter chains of sugars called oligosaccharides. Thus, the presently disclosed method and apparatus are believed suitable to produce α-Amylase, among other enzymes, and to use fungi to produce various products 38.

Enzymes made from fungus are also used in laundry detergents, pulp and paper processing, biopolymers, chemical synthesis, animal feed, sugar reductions and in the production of oil, gas and ethanol. Thus, the presently disclosed method and apparatus are believed suitable to use fungi to produce enzyme products 38 suitable for use in these, and other, consumer products.

Cells 36 that include insect cells (e.g., Sf9, HiFive etc.) may be used to secrete proteins, peptides and various vaccines. Illustrative uses include infecting cultured insect cells with a recombinant baculovirus to product a protein product 38 as described in U.S. Pat. No. 4,879,236, the complete contents of which are incorporated herein by reference. Likewise, insect cells may be used to produce a recombinant baculovirus capable of expressing a selected gene in the host insect cell as described in U.S. Pat. No. 4,745,051, the complete contents of which are incorporated herein by reference. Similarly, SF9 cells infected by recombinant baculovirus are believed suitable to express human transferring protein. Insect cells may also be used to produce Interleukin-2. Expression from baculovirus has been used to produce influenza vaccines (seasonal and pandemic), human papillomavirus, pathogens, therapeutic vaccines for oncology (prostate and breast cancer) and diabetes, and products for gene therapy for lipoprotein lipase deficiency. Other proteins secreted from cells include amino acid constituents and vaccines, including the human papilloma virus vaccine, as product 38 believed recoverable using the presently disclosed method and apparatus.

Cells 36 that include algae may be used to produce a variety of products. For example, using cyanobacteria to express various oils, hydrocarbon-based products, lipids, sugars and lactic acid is known. Engineered cyanobacterium that includes a recombinant acyl-ACP reductas enzyme and a recombinant alkanal decarboxylative monooxygenase enzyme, at least one of which is heterologous with respect to the engineered cyanobacterium may be cultured in the presence of light and carbon dioxide to produce n-alkanes, such as n-pentadecane, as described more fully in U.S. Pat. No. 8,043,840, the complete contents of which are incorporated herein by reference. Cells 36 that include these algae are believed suitable with the presently disclosed method and apparatus to produce the above identified products, among others.

The above description is given by way of example, and not limitation. Given the above disclosure, one skilled in the art could devise variations that are within the scope and spirit of the invention disclosed herein, including using various porosities on the filters 74 and/or frit 76 to accommodate different sizes of product 38. The above apparatus and method is described for use in separating product expressed from cells of living organisms where the product has a size that is smaller than the cells, cell fragments and usually the growth media in which the cells are grown. Preferably, the product is at least 10 times smaller in its larges dimension than the vast majority of small particles of debris in the container 32 in which the product 38 is produced. But the cap and filter mechanism and the associated method of use are equally applicable to separating other small, desirable products from surrounding debris. Thus, this method is not limited to the preferred cellular products. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A cap and filter step reduction tool assembly for use in separating product excreted externally of living cells from liquids, growth media and debris in which the product exists within a container, the container having a neck defining an opening to the container, the product having a size measured by molecular weight, comprising:
   a cap having a first portion configured to cover the opening of the container, an outlet and a filter assembly located therebetween, the filter assembly comprising:
      a filter housing having a porous support with a rim around a periphery of the porous support;
      a graded porosity filter fitting within that rim and having a small pore size sufficiently large to pass the product through the filter while retaining the debris;
      a locking ring urging a periphery of the filter against an outer portion of the filter; and
      a frit located to place the filter between the porous support and the frit, the frit being sealed to the housing so fluid flows through the frit and to the filter during use;
      a vent opening extending through the cap with a vent tube connected to the portion of the cap defining the vent opening, the vent tube having a length selected to extend into an ullage of the container when the container is inverted so product flows from the container through the filter and outlet of the cap.

2. The cap and filter step reduction tool assembly of claim 1, wherein the graded porosity filter comprises one of a plurality of planar filters of different porosity or a plurality of lenticular filters.

3. The cap and filter step reduction tool assembly of claim 2 wherein the locking ring has at least one annular rib around a periphery of the locking ring and located to abut an upstream surface of the filter during use, and wherein the cap has at least one annular rib around a periphery of the cap and located to abut a downstream surface of the filter during use.

4. The cap and filter step reduction tool assembly of claim 2, wherein the filter assembly is press fit into a cylindrical recess in the cap formed by a cylindrical sidewall of the cap, which cylindrical recess is located downstream of a threaded skirt configured to threadingly engage the container.

5. The cap and filter step reduction tool assembly of claim 4, wherein an inner surface of the flat, annular periphery abuts the filter housing.

6. The cap and filter step reduction tool assembly of claim 2, wherein the vent opening comprises a tubular fitting extending from opposing surfaces of the cap.

7. The cap and filter step reduction tool assembly of claim 2, further comprising a source of positive pressure in fluid communication with the vent opening so as to provide a positive pressure to the inside of the container during use of the cap and filter step reduction tool.

8. The cap and filter step reduction tool assembly of claim 2, wherein the filters are selected to pass product having a molecular weight from 10,000 to 3,000,000 MW.

9. The cap and filter step reduction tool assembly of claim 2, wherein the filters are selected to pass product having a molecular weight from about 100-10,000 MW.

10. The cap and filter step reduction tool assembly of claim 2, wherein the filters are selected to pass product having a molecular weight from about 100-150 MW.

11. The cap and filter step reduction tool assembly of claim 2, wherein the first portion of the cap is connected to the opening of the container, the container containing mammalian cells and growth media.

12. The cap and filter step reduction tool assembly of claim 2, wherein the first portion of the cap is connected to the opening of the container, the container containing insect cells and growth media.

13. The cap and filter step reduction tool assembly of claim 2, wherein the first portion of the cap is connected to the opening of the container, the container containing algae or cyanobacteria cells and growth media.

14. The cap and filter step reduction tool assembly of claim 1 wherein the locking ring has at least one annular rib around a periphery of the locking ring and located to abut an upstream surface of the filter during use, and wherein the cap has at least one annular rib around a periphery of the cap and located to abut a downstream surface of the filter during use.

15. The cap and filter step reduction tool assembly of claim 1, wherein the filter assembly is press fit into a cylindrical recess in the cap formed by a cylindrical sidewall of the cap.

16. The cap and filter step reduction tool assembly of claim 1, wherein the filter assembly is press fit into a cylindrical recess in the cap formed by a cylindrical sidewall of the cap, which cylindrical recess is located downstream of a threaded skirt configured to threadingly engage the container.

17. The cap and filter step reduction tool assembly of claim 16, wherein the cylindrical recess has a flat, annular periphery with an inner portion that tapers to an outlet fitting forming the outlet therein.

18. The cap and filter step reduction tool assembly of claim 1, wherein the graded porosity filter comprises a plurality of filters, each with a different porosity.

19. The cap and filter step reduction tool assembly of claim 1, wherein the frit comprises a graded porosity filter having an interstitial pore spacing that decreases in the downstream direction.

20. The cap and filter step reduction tool assembly of claim 1, further comprising a purification column in fluid communication with the outlet of the cap.

21. The cap and filter step reduction tool assembly of claim 1, wherein the first portion of the cap is a cylindrical flange and the outlet is a tube having a longitudinal axis coinciding with the longitudinal axis of the filter assembly but offset from a longitudinal axis of the cylindrical flange.

22. The cap and filter step reduction tool assembly of claim 1, further comprising a purification column in fluid communication with the outlet of the cap, with a vacuum port downstream of the filter assembly in order to apply a negative pressure to the fluid in the container during use of the cap and filter step reduction tool.

23. The cap and filter step reduction tool assembly of claim 1, wherein the first portion of the cap is connected to the opening of the container, the container containing living cells and growth media.

24. The cap and filter step reduction tool assembly of claim 1, wherein the graded porosity filter is configured to retain filter media larger in size than the product.

25. The cap and filter step reduction tool assembly of claim 1, wherein the graded porosity filter comprises at least one graded porosity filter having an interstitial pore spacing that decreases in the downstream direction.

26. A kit for transferring fluid from a container having a neck defining an opening to the container, the container having therein a product excreted externally of living cells that were contained in a growth media in the container, the container further containing fragments of those cells, the product having a size measured by molecular weight, comprising:
- a cap having a first portion configured to cover the opening of the container, an outlet and a filter assembly located there between, the filter assembly comprising:
  - a filter housing having a porous support with a rim around a periphery of the porous support;
  - a filter fitting within that rim and having a small pore size sufficiently large to pass the product through the filter while retaining the debris, the filter comprises a graded porosity filter;
  - a locking ring urging a periphery of the filter against an outer portion of the filter; and
  - a frit located to place the filter between the porous support and the frit, the frit and locking ring being sealed to each other and the filter housing so that fluid flows through the frit and then through the filter and out the cap outlet during use; and
- a vent opening extending through the cap;
- a vent tube having a first end configured to be connected to the portion of the cap defining the vent opening, the vent tube having a length selected to extend into an ullage of the container when the container is inverted so product flows from the container through the outlet of the cap.

27. The kit of claim 26, further including a fluid communication assembly comprising:
- a first fluid transfer tube having one end configured to be connected to the outlet of the cap;
- a fluid flow control valve configured to be placed in fluid communication with the first tube either directly or through intervening fluid connections; and
- a second tube having a first end configured to be placed in fluid communication with a downstream end of the valve either directly or through intervening fluid connections, and having a second end configured to connect to one of a Luer lock or an inlet of a purification column.

28. The kit of claim 26, wherein the graded porosity filter is configured to retain filter media larger in size than the product.

29. A cap and filter step reduction tool assembly for use in separating product excreted externally of living cells from liquids, growth media and debris in which the product exists within a container, the container having a neck defining an opening to the container, the product having a size measured by molecular weight, comprising:
- a cap having a first portion configured to cover the opening of the container, an outlet and a filter assembly located therebetween, the filter assembly comprising:
  - a filter housing having a porous support with a rim around a periphery of the porous support;
  - a graded porosity filter fitting within that rim and having a small pore size sufficiently large to pass the product through the graded porosity filter while retaining the debris;
  - a locking ring urging a periphery of the graded porosity filter against an outer portion of the graded porosity filter;
  - wherein the graded porosity filter comprises one of a plurality of planar filters of different porosity or a plurality of lenticular filters and wherein the first portion of the cap is connected to the opening of the container, the container containing mammalian cells and growth media.

30. The cap and filter step reduction tool assembly of claim 29, wherein the filter comprises a plurality of planar filters of different porosity.

31. A cap and filter step reduction tool assembly for use in separating product excreted externally of living cells from liquids, growth media and debris in which the product exists within a container, the container having a neck defining an opening to the container, the product having a size measured by molecular weight, comprising:
- a cap having a first portion configured to cover the opening of the container, an outlet and a filter assembly located therebetween, the filter assembly comprising:
  - a filter housing having a porous support with a rim around a periphery of the porous support;
  - a graded porosity filter fitting within that rim and having a small pore size sufficiently large to pass the product through the graded porosity filter while retaining the debris;
  - a locking ring urging a periphery of the graded porosity filter against an outer portion of the graded porosity filter;
  - wherein the graded porosity filter comprises one of a plurality of planar filters of different porosity or a plurality of lenticular filters and wherein the first portion of the cap is connected to the opening of the container, the container containing insect cells and growth media.

32. The cap and filter step reduction tool assembly of claim 31, wherein the filter comprises a plurality of planar filters of different porosity.

33. A cap and filter step reduction tool assembly for use in separating product excreted externally of living cells from liquids, growth media and debris in which the product exists within a container, the container having a neck defining an opening to the container, the product having a size measured by molecular weight, comprising:
- a cap having a first portion configured to cover the opening of the container, an outlet and a filter assembly located therebetween, the filter assembly comprising:
  - a filter housing having a porous support with a rim around a periphery of the porous support;
  - a graded porosity filter fitting within that rim and having a small pore size sufficiently large to pass the product through the graded porosity filter while retaining the debris;
  - a locking ring urging a periphery of the graded porosity filter against an outer portion of the graded porosity filter;
  - wherein the graded porosity filter comprises one of a plurality of planar filters of different porosity or a plurality of lenticular filters and wherein the first portion of the cap is connected to the opening of the container, the container containing algae or cyanobacteria cells and growth media.

34. The cap and filter step reduction tool assembly of claim 33, wherein the filter comprises a plurality of planar filters of different porosity.

35. A cap and filter step reduction tool assembly for use in separating product excreted externally of living cells from liquids, growth media and debris in which the product exists within a container, the container having a neck defining an opening to the container, the product having a size measured by molecular weight, comprising:
- a cap having a first portion configured to cover the opening of the container, an outlet and a filter assembly located therebetween, the filter assembly comprising:
  - a filter housing having a porous support with a rim around a periphery of the porous support;

a graded porosity filter fitting within that rim and having a small pore size sufficiently large to pass the product through the graded porosity filter while retaining the debris;

a locking ring urging a periphery of the graded porosity filter against an outer portion of the graded porosity filter;

wherein the graded porosity filter comprises one of a plurality of planar filters of different porosity or a plurality of lenticular filters and wherein the first portion of the cap is connected to the opening of the container, the container containing living cells and growth media.

36. The cap and filter step reduction tool assembly of claim 35, wherein the filter comprises a plurality of planar filters of different porosity.

* * * * *